(12) United States Patent
Brambilla et al.

(10) Patent No.: US 10,993,916 B2
(45) Date of Patent: *May 4, 2021

(54) CRYSTALLINE MICROPARTICLES OF A BETA-AGONIST COATED WITH A FATTY ACID

(71) Applicant: Chiesi Farmaceutici S.p.A., Parma (IT)

(72) Inventors: Gaetano Brambilla, Parma (IT); Paolo Colombo, Parma (IT); Francesca Buttini, Parma (IT); Michele Miozzi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 135 days.

This patent is subject to a terminal disclaimer.

(21) Appl. No.: 15/152,835

(22) Filed: May 12, 2016

(65) Prior Publication Data

US 2016/0324792 A1    Nov. 10, 2016

Related U.S. Application Data

(62) Division of application No. 13/649,336, filed on Oct. 11, 2012, now abandoned.

(30) Foreign Application Priority Data

Oct. 11, 2011    (EP) .................................... 11184687

(51) Int. Cl.

| | |
|---|---|
| *A61K 9/50* | (2006.01) |
| *A61K 9/00* | (2006.01) |
| *A61K 31/167* | (2006.01) |
| *A61K 31/137* | (2006.01) |
| *A61M 11/02* | (2006.01) |
| *B01J 2/02* | (2006.01) |
| *A61K 9/16* | (2006.01) |
| *A61K 31/4704* | (2006.01) |
| *A61M 15/00* | (2006.01) |

(52) U.S. Cl.
CPC ............ *A61K 9/5015* (2013.01); *A61K 9/008* (2013.01); *A61K 9/5089* (2013.01); *A61K 31/137* (2013.01); *A61K 31/167* (2013.01); *A61K 31/4704* (2013.01); *A61M 11/02* (2013.01); *A61M 15/009* (2013.01); *A61M 15/0068* (2014.02); *B01J 2/02* (2013.01); *A61K 9/1617* (2013.01); *A61M 2202/064* (2013.01)

(58) Field of Classification Search
None
See application file for complete search history.

(56) References Cited

U.S. PATENT DOCUMENTS

| | | | |
|---|---|---|---|
| 4,259,905 A * | 4/1981 | Abiko | .................... B41N 1/003 |
| | | | 101/465 |
| 4,279,757 A * | 7/1981 | DeBeuckelaer | ... B01D 17/0202 |
| | | | 210/671 |
| 5,182,097 A | 1/1993 | Byron et al. | |
| 6,221,398 B1 | 4/2001 | Jakupovic et al. | |
| 6,524,557 B1 | 2/2003 | Backstrom et al. | |
| 2003/0180283 A1 | 9/2003 | Batycky et al. | |
| 2004/0013611 A1 | 1/2004 | Schultz et al. | |
| 2004/0101483 A1 | 5/2004 | Muller-Walz et al. | |
| 2005/0106335 A1* | 5/2005 | Badyal | ..................... C09D 4/00 |
| | | | 428/2 |
| 2006/0009410 A1 | 1/2006 | Crooke et al. | |
| 2006/0286038 A1 | 12/2006 | Rairkar et al. | |
| 2007/0009445 A1 | 1/2007 | Eck | |
| 2009/0215732 A1 | 8/2009 | Eriksson et al. | |
| 2010/0047296 A1* | 2/2010 | Banowski | ............ A61K 8/0229 |
| | | | 424/401 |
| 2011/0150782 A1 | 6/2011 | Bonelli et al. | |

FOREIGN PATENT DOCUMENTS

| | | |
|---|---|---|
| EP | 2050437 A1 * | 4/2009 |
| WO | WO 91/04011 | 4/1991 |
| WO | WO 03/020253 | 3/2003 |
| WO | WO 2010/007447 | 1/2010 |

OTHER PUBLICATIONS

Da Rocha et al. Science and technology of pressurized metered-dose inhalers "Controlled Pulmonary Drug Delivery" Smyth et al. ed. Controlled Release Society:New York 2011 p. 165, 170.*
European Search Report in Application No. 11184687.9 dated Mar. 28, 2012.
Vervaet et al., International Journal of Pharmaceutics (1999) 186: 13-30.
Frijlink et al., Expert Opinion in Drug Delivery, (2004) 1(1):67-86.

* cited by examiner

*Primary Examiner* — Robert A Wax
*Assistant Examiner* — Caralynne E Helm
(74) *Attorney, Agent, or Firm* — Oblon, McClelland, Maier & Neustadt, L.L.P.

(57) ABSTRACT

Crystalline microparticles consisting of a phenylalkylamino beta$_2$-adrenergic agonist coated with a C12-C20 fatty acid are useful for the preparation of pharmaceutical aerosol formulations in form of suspension in a liquefied propellant gas or powder formulations.

3 Claims, 1 Drawing Sheet

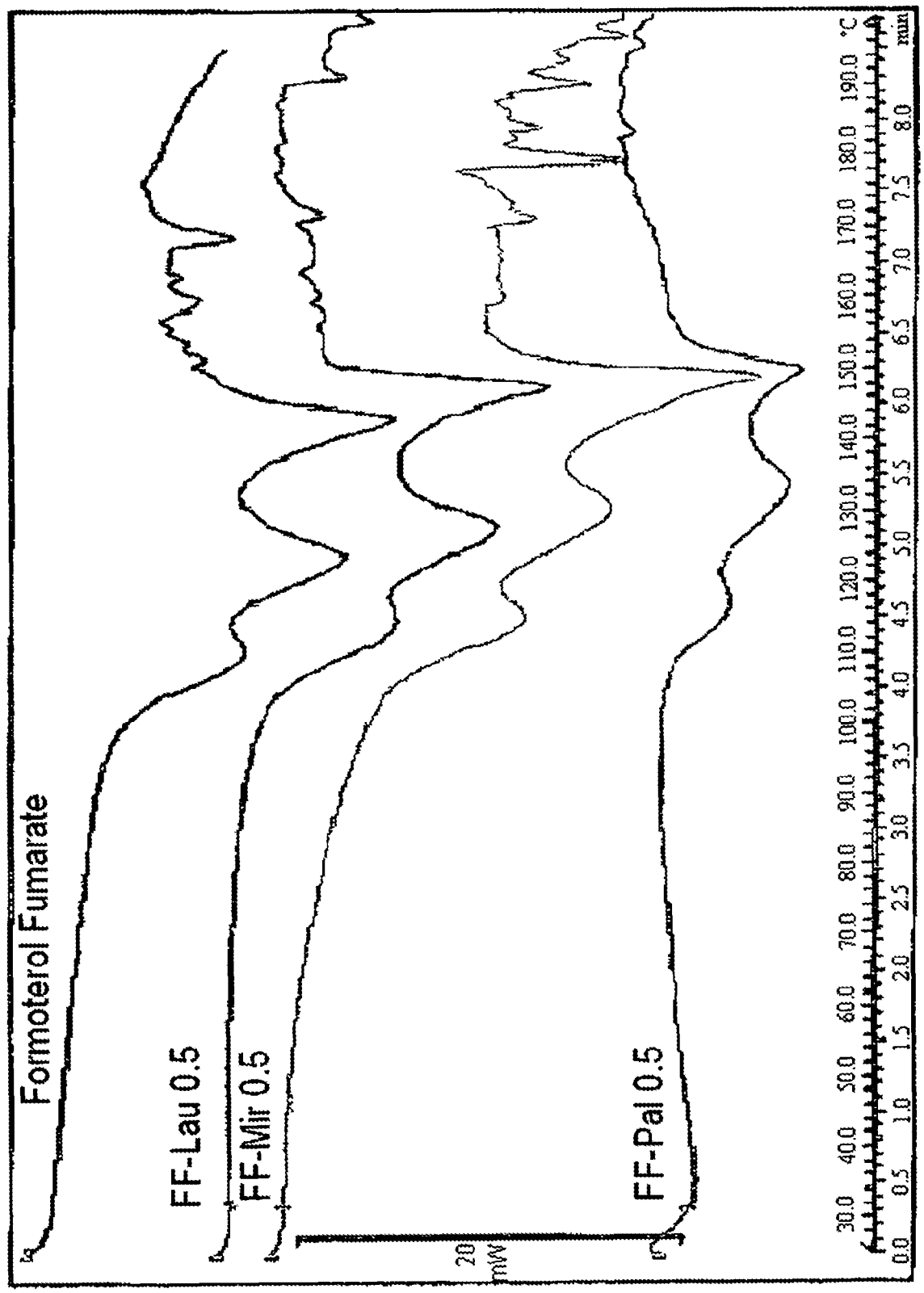

CRYSTALLINE MICROPARTICLES OF A BETA-AGONIST COATED WITH A FATTY ACID

CROSS REFERENCES TO RELATED APPLICATIONS

This application is a division of U.S. patent application No. 13/649,336, filed Oct. 11, 2012, the disclosure of which is incorporated herein by reference in its entirety. This application claims priority to European Patent Application No. 11184687.9, filed Oct. 11, 2011, the disclosure of which is incorporated herein by reference in its entirety.

BACKGROUND OF THE INVENTION

Field of the Invention

The present invention relates to crystalline microparticles comprising a beta$_2$-agonist suitable for use in formulations to be administered by inhalation for the treatment of respiratory diseases. The present inventions also relates to pharmaceutical aerosol formulations comprising said microparticles and to a process for preparing them. The present invention further relates to methods of treating/preventing certain diseases and conditions by administering such microparticles.

Discussion of the Background

The administration of pharmacologically active ingredients by inhalation to the lungs is a widely used technique especially for the treatment of reversible airway obstruction, inflammation and hyper-responsiveness. Inhalable preparations include dry powders formulations, pressurized metered dose (pMDI) formulations containing propellants such as hydrofluoroalkanes (HFA), or propellant-free aqueous formulations to be administered by suitable devices such as nebulizers.

The drugs present in the formulations can either be dissolved or suspended. A specific group of drugs administered by the pulmonary route are bronchodilators having a local therapeutic action in the lungs and/or a systemic therapeutic action after absorption in the blood.

For example, widely used bronchodilators are beta2-agonists belonging to the class of the phenylalkylamino derivatives such as rac-(R,R)-N-[2-hydroxy-5-[1-hydroxy-2-[1-(4-methoxyphenyl) propan-2-ylamino]ethyl]phenyl] formamide, also known as formoterol. However, formoterol as well as other drugs belonging to said class may suffer of chemical stability problems due to the susceptibility to oxidative conditions of the functional groups present on the molecules such as formamide and hydroxyethyl groups. Some of said groups such as formamide are also susceptive to solvolysis reactions.

On the other hand, molecules belonging to said class may also incur problems of physical stability of their suspension formulations. This is because of partial solubility of the drugs in the liquefied gas propellant. This partial solubility, in turn, may lead to an undesirable increase in the particle size during storage and/or the formation of aggregates.

Moreover, formulations of beta$_2$-agonists in HFA propellant might be susceptible to absorption of the drug into the rubber components of the valves of the administration device. This may then cause the valves to seize resulting in a reduction of fine particle mass and/or the aggregates of particles will penetrate less well into the fine lower respiratory pathways, subsequently causing problems with dose uniformity.

To overcome the problems of physical stability and of adsorption of the drug, it has been proposed in the art to coat the particles with additives such as surfactants, and to suspend said coated particles in the HFA propellant. For instance, WO 92/08447 and WO 91/04011 teach coating the active agent by a process involving the steps of dissolving the surfactant in a solvent in which the pharmaceutically active agent is substantially insoluble, mixing a quantity of the pharmaceutically active agent, in micronized form, into the surfactant solution and isolating particles of surfactant coated active agent either by filtration and drying, or by removal of the solvent by evaporation. However, it has so far not proven possible, to manufacture useful formulations in this way. For example, it is difficult to achieve a uniform coating using techniques of this nature because the manner in which the surfactant agent precipitates from the evaporating solvent can be unpredictable.

WO 2006/059152 discloses the preparation of coated particles with dispersing agents such as surfactants by mechano-fusion processes. However, it is known that particles obtained in this way are prevalently amorphous. On the other hand, amorphous or prevalently amorphous materials tend to absorb water in larger amounts than crystalline ones, and this could be a pitfall for active ingredients liable to degradation by hydrolysis.

WO 00/61108 discloses salmeterol particles coated with a surfactant and free of any other coating excipient. They are obtained by a process involving the steps of suspending the active ingredient in form of particles in a medium, preferably water, then dispersing the surfactant, and subjecting the suspension to spray-drying. However, also in this case, it is well known that the use of water could yield some amorphous material. Moreover, it is difficult to achieve a uniform coating if the surfactant is dispersed and not dissolved in said medium.

WO 2008/152398 discloses particles coated with polymers such as PVP without any mention of their chemical stability.

US 2004/101483 discloses suspension aerosol formulations based on hydrofluoroalkanes comprising micronized particles of active ingredients and calcium salts, magnesium salts, and zinc salts of palmitic acid and of stearic acid as solid excipients. The demonstrated advantage is that said suspensions show a markedly improved valve accessibility.

US 2004/013611 discloses suspension aerosol formulations comprising a therapeutically effective amount of micronized albuterol sulfate, from about 5 to 15 percent by weight of ethanol, from about 0.05 to about 0.5 percent by weight of a surfactant selected from the group consisting of oleic acid and sorbitan trioleate, and HFC 227 as substantially the only propellant. Said formulations are characterized in that they exhibit substantially no growth in particle size or change in crystal morphology of the drug over a prolonged period, are substantially and readily redispersible, and upon redispersion do not flocculate so quickly as to prevent reproducible dosing of the drug. Nothing is said about their chemical stability.

In view of the above, there is still a need for particles of beta$_2$-agonists of high chemical stability as well as being capable of giving rise to physically stable suspensions with a slow sedimentation rate and a reduced adhesion to the components of the device. These problems are solved by the particles of the present invention.

SUMMARY OF THE INVENTION

Accordingly, it is one object of the present invention to provide novel particles of beta$_2$-agonists.

It is another object of the present invention to provide novel beta$_2$-agonists which exhibit high chemical stability.

It is another object of the present invention to provide novel beta$_2$-agonists which are capable of giving rise to physically stable suspensions with a slow sedimentation rate and a reduced adhesion to the components of a device in which they are contained.

It is another object of the present invention to provide novel methods of preparing such particles.

It is another object of the present invention to provide novel methods of treating and/or preventing certain diseases and conditions by administering such particles.

These and other objects, which will become apparent during the following detailed description, have been achieved by the inventors' discovery of crystalline microparticles consisting of a phenylalkylamino beta$_2$-adrenergic agonist coated with a C12-C20 fatty acid in an amount comprised between 0.2 and 2.5% by weight.

Thus, in a first aspect, the invention is directed to crystalline microparticles comprising a phenylalkylamino beta$_2$-adrenergic agonist coated with a C12-C20 fatty acid in an amount comprised between 0.2 and 2.5% by weight.

In a second aspect, the crystalline microparticles preferably consist of a phenylalkylamino beta$_2$-adrenergic agonist coated with a C12-C20 fatty acid in an amount comprised between 0.2 and 2.5% by weight.

Advantageously, said beta$_2$-agonist is selected from a derivative belonging to the general formula (I):

$$HO-\overset{R_4}{\underset{\underset{H}{N}}{C}}-\overset{}{\underset{R_3}{C}}-(CH_2)m-A-(CH_2)n-B-(CH_2)p-\text{Ar}\quad (I)$$

wherein $R_1$ is $CH_2OH$ or $NHCOR_{10}$
with the proviso that, when $R_1$ is $CH_2OH$, $R_2$ is hydrogen, while, when $R_1$ is $NHCOR_{10}$, $R_2$ and $R_{10}$ can be independently hydrogen or form together a vinylene (—CH=CH—) or ethoxy (—CH$_2$—O—) radical;

m is an integer from 0 to 5, preferably 0 or 5;
n is an integer from 0 to 4, preferably 0, 2 or 4;
p is an integer from 0 to 2, preferably 0 or 1;
A represents oxygen or a bond;
B represents oxygen or a bond;
$R_3$ and $R_4$ are hydrogen or methyl; otherwise, when m is 1, n, p are 0, A and B are bonds, and $R_3$ is hydrogen, $R_4$ can form with $R_5$ a methylene bridge —(CH$_2$)q- where q is 1 or 2, preferably 1;
$R_5$, $R_6$, $R_7$, $R_8$, and $R_9$, which are the same or different, are each independently selected from hydrogen, hydroxyl, $C_1$-$C_4$ alkyl, $C_1$-$C_4$ alkoxy, halogen atoms, $SO_2NH_2$, and 2-hydroxy-2-phenyl-ethylamino; preferably they are hydrogen, halogen atoms, $C_1$-$C_4$ alkyl, and $C_1$-$C_4$ alkoxy,
and pharmaceutically acceptable salts and/or solvates thereof.

In a third aspect, the invention provides pharmaceutical aerosol formulations for pressurized metered dose inhalers (pMDIs) comprising the above microparticles in suspension in a liquefied propellant gas.

In a fourth aspect, the invention provides pressurized metered dose inhalers (pMDI) comprising a canister filled with the aforementioned aerosol pharmaceutical formulation, and a metering valve for delivering a daily therapeutically effective dose of the active ingredient.

In a fifth aspect, the invention concerns dry powder pharmaceutical formulations comprising the above microparticles and, optionally a carrier.

In a sixth aspect, the invention provides dry powder inhalers filled with the aforementioned dry powder formulation.

In a seventh aspect, the present invention is directed to a process for preparing the microparticles of the invention, said process comprising the steps of:

(a) preparing a solution of the C12-C20 fatty acid in a fluorinated model propellant wherein the beta$_2$-agonist is substantially insoluble selected from the group of perfluoropentane, 2H,3H-perfluoropentane (HPFP), perfluorohexane, and 1H-perfluorohexane;

(b) adding the micronized drug powder to the solution of the fatty acid;

(c) stirring to give a homogeneous suspension; and (d) subjecting the resulting suspension to spray-drying to obtain the coated microparticles.

In an eighth aspect, the present invention is also directed to the microparticles of the invention for use for the prevention and/or treatment of a respiratory disease.

In an ninth aspect, the present invention is further directed to the use of the microparticles of the invention in the manufacture of a medicament for the prevention and/or treatment of a respiratory disease.

In a tenth aspect, the present invention provides methods for preventing and/or treating a respiratory disease in a patient, comprising administering a therapeutically effective amount of the microparticles of the invention.

In an eleventh aspect, the present invention concerns crystalline microparticles consisting of a phenylalkylamino beta$_2$-adrenergic agonist coated with a C12-C20 fatty acid in an amount comprised between 0.2 and 2.5% by weight, said microparticles obtainable by a process comprising the steps of:

(a) preparing a solution of the C12-C20 fatty acid in a fluorinated model propellant wherein the beta$_2$-agonist is substantially insoluble selected from the group of perfluoropentane, 2H,3H-perfluoropentane (HPFP), perfluorohexane, and 1H-perfluorohexane;

(b) adding the micronized drug powder to the solution of the fatty acid;

(c) stirring to give a homogeneous suspension; and (d) subjecting the resulting suspension to spray-drying to obtain the coated microparticles.

In a further aspect, the present invention provides a process for preparing crystalline microparticles consisting of a drug to be administered by inhalation coated with a C12-C20 fatty acid, said process comprising the steps of:

(a) preparing a solution of the C12-C20 fatty acid in a fluorinated model propellant wherein the drug is substantially insoluble selected from the group of perfluoropentane, 2H,3H-perfluoropentane (HPFP), perfluorohexane, and 1H-perfluorohexane;

(b) adding the micronized drug powder to the solution of the fatty acid;

(c) stirring to give a homogeneous suspension; and (d) subjecting the resulting suspension to spray-drying to obtain the coated microparticles.

The invention is also directed to the crystalline coated microparticles obtainable by said process.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 is a thermogram of microparticles of the present invention in comparison to crystalline microparticles of formoterol fumarate dihydrate (top line).

DETAILED DESCRIPTION OF THE PREFERRED EMBODIMENTS

The term "halogen atoms" as used herein includes fluorine, chlorine, bromine and iodine.

The expression "$C_1$-$C_4$ alkyl" refers to straight-chained and branched alkyl groups wherein the number of carbon atoms is in the range 1 to 4. Particular alkyl groups are methyl, ethyl, n-propyl, isopropyl and t-butyl, preferably methyl and ethyl.

The expression "$C_1$-$C_4$ alkoxy" refers to straight and branched chain alkoxy groups wherein the number of carbon atoms is in the range 1 to 4. Exemplary groups are methoxy, ethoxy, and butyloxy.

The term "coated" refers to microparticles having their surface covered by a continuous film of the fatty acid.

The term "single therapeutically effective dose" means the quantity of active ingredient administered at one time by inhalation upon actuation of the pMDI or DPI inhaler.

Said dose may be delivered in one or more actuations, preferably one actuation (shot) of the inhaler.

The term "actuation" refers to the release of active ingredient from the device by a single activation (e.g. mechanical or breath).

For "fluorinated model propellant" it is meant a fluorinated alkane derivative liquid at room temperature and at atmospheric pressure in which common beta$_2$-agonists are insoluble. Typical members of this class are perfluoropentane, 2H,3H-perfluoropentane, perfluorohexane, and 1H-perfluorohexane. 2H,3H-perfluoropentane is also known as HPFP (see Rogueda P. *Drug Dev. Ind. Pharm.*, 2003, 29(1), 39-49, which is incorporated herein by reference in its entirety).

"Substantially insoluble" refers to an active ingredient having a solubility in the desired medium of less than 1.0% w/v, preferably of less than 0.5%, more preferably less than 0.1% w/v.

In general terms, the particle size of the particles is quantified by measuring a characteristic equivalent sphere diameter, known as volume diameter, by laser diffraction. The particle size can also be quantified by measuring the mass diameter by means of suitable instruments and techniques known to the skilled person, such as sieving.

The volume diameter (VD) is related to the mass diameter (MD) by the density of the particles (assuming the size being independent from the density of the particles).

In the present application, the particle size interval is expressed in terms of mass diameter. Otherwise, the particle size distribution is expressed in terms of: i) the volume median diameter (VMD) which corresponds to the diameter of 50 percent by weight or volume respectively, of the particles, e.g. d(v0.5), and ii) the volume diameter (VD) in microns of 10% and 90% of the particles, respectively, e.g. d(v0.1) and d(v0.9).

Upon aerosolization, the particle size is expressed as mass aerodynamic diameter (MAD) and the particle size distribution as mass median aerodynamic diameter (MMAD). The MAD indicates the capability of the particles of being transported as suspended in an air stream. The MMAD corresponds to the mass aerodynamic diameter of 50 percent by weight of the particles.

The expression "physically stable" refers to formulations which exhibit substantially no growth in particle size or change in crystal morphology of the suspended particles over a prolonged period, are readily redispersible, and upon redispersion, do not flocculate so quickly as to prevent reproducing dosing of the active ingredient.

The expression "chemically stable" refers to a formulation that, upon storage, meets the requirements of the EMEA Guideline CPMP/QWP/122/02 referring to "Stability Testing of Existing Active Substances and Related Finished Products".

The expression "respirable fraction" refers to an index of the percentage of active particles which would reach the deep lungs in a patient.

The respirable fraction, also termed fine particle fraction (FPF), is evaluated using a suitable in vitro apparata such as Next Generation Impactor (NGI), Multistage Cascade Impactor or Multi Stage Liquid Impinger (MLSI) according to procedures reported in common Pharmacopoeias. It is calculated by the ratio between the delivered dose and the fine particle mass (formerly fine particle dose).

The delivered dose is calculated from the cumulative deposition in the apparatus, while the fine particle mass is calculated from the deposition on Stage N (herein N is an integer number) to filter (AF) corresponding to particles ≤5.0 microns.

The term "therapeutically effective amount" means the amount of active ingredient that, when delivered to the lungs, provides the desired biological effect.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

The present invention concerns crystalline microparticles comprising or consisting of a phenylalkylamino beta$_2$-adrenergic agonist and pharmaceutically acceptable salts and/or solvates thereof.

Phenylalkylamino beta$_2$-adrenergic agonists are drugs having a bronchodilator activity and include for example salbutamol (albuterol), bambuterol fenoterol, procaterol, salmeterol, indacaterol, and formoterol.

Pharmaceutically acceptable salts include those obtained by reacting the amino group of the compound with an inorganic or organic acid to form a salt, for example, hydrochloride, hydrobromide, sulphate, phosphate, methane sulfonate, camphor sulfonate, oxalate, maleate, fumarate, succinate, citrate, cinnamate, xinafoate, and trifenatate.

Advantageously, said beta$_2$-agonist is selected from a derivative belonging to the general formula (I).

The compounds of general formula (I) may contain asymmetric centers.

Therefore the present invention includes all the optical stereoisomers and mixtures thereof.

A first class of preferred compounds is that wherein $R_1$ is $NHCOR_{10}$ with $R_{10}$=H, $R_4$ is methyl, m is 1, n, p are 0, A and B are bonds, $R_3$, $R_5$, $R_6$, $R_8$ and $R_9$ are H, and $R_7$ is methoxy.

When the phenolic group is adjacent to $R_1$, the compound is known as formoterol.

As it contains two chiral centers, formoterol is preferably used in the form of 1:1 (R,R), (S,S) racemate or (R,R) enantiomer, more preferably as the racemate.

A particularly preferred salt is the fumarate dihydrate.

A second class of preferred compounds is that wherein:
$R_1$ is $NHCOR_{10}$ wherein $R_{10}$ forms together with $R_2$ a vinylene (—CH=CH—) radical, $R_1$ is H, $R_3$ forms with $R_5$ a methylene bridge —$(CH_2)q$- with q=1, m is 1, n, p are 0, A and B are bonds, R6 and $R_9$ are H and $R_7$ and $R_8$ are ethyl group.

When the phenolic group is adjacent to $R_1$, the compound is known as indacaterol.

Since it contains a chiral center, indacaterol is preferably used in the form of R-enantiomer, more preferably as maleate salt.

A third class of preferred compounds is that wherein:
$R_1$ is $CH_2OH$, $R_2$ $R_6$, $R_7$ and $R_8$ are H, $R_5$ and $R_9$ are chlorine atoms, A and B are O, m is 5, n is 2, and p is 1.

When the phenolic group is adjacent to $R_1$, the compound is known as vilanterol. Vilanterol is preferably used in the form of R-enantiomer as trifenatate salt A fourth class of preferred compounds is that wherein:
$R_1$ is $NHCOR_{10}$ with $R_{10}$ forming together with $R_2$ an ethoxy (—CH2-O—) radical, $R_3$ and $R_4$ are methyl, m=1, A d B are bonds, n and p are 0, $R_5$, $R_6$, $R_8$ and $R_9$ are H, and $R_7$ is methoxy. When the phenolic group is meta to $R_1$ the compound is known as olodaterol, that is preferably used as R-enantiomer.

A fifth class of preferred compounds is that wherein:
$R_1$ is $NHCOR_{10}$ with $R_{10}$=H, $R_2$, $R_3$, $R_4$, $R_5$, $R_6$, $R_8$ and $R_9$ are H, m is 1, A and B are bonds, n and p are 0, and $R_7$ is 2-hydroxy-2-phenyl-ethylamino.

When the phenolic group is adjacent to $R_1$ the compound is known as milveterol. As it contains two chiral centers, milveterol is preferably used in the form of (R,R)-enantiomer, more preferably as the hydrochloride salt.

A sixth class of preferred compounds is that wherein:
$R_1$ is $CH_2OH$, $R_2$, $R_3$, $R_4$, $R_5$, $R_6$, $R_8$ and $R_9$ are H, m is 5, n is 4, p is 0, A is O, and B is a bond.

When the phenolic group is adjacent to $R_1$ the compound is known as salmeterol. As it contains one chiral center, salmeterol is preferably used in the form of racemic form (R,S), more preferably as a xinafoate salt.

Preferably, the compound of formula (I) is a long-acting $beta_2$-agonist selected from the group consisting of formoterol, salmeterol, vilanterol, olodaterol, milveterol, indacaterol, and pharmaceutically acceptable salts and/or solvates thereof.

In a particular embodiment, preferred compounds are those wherein $R_1$ is $NHCOR_{10}$, $R_2$ and $R_{10}$ are H, and the other substituents and indexes have the meanings reported above.

In fact, phenylalkylamino derivatives bearing said group are particularly sensitive to solvolysis reactions.

The preferred compound of said class is formoterol, preferably in the form of fumarate dihydrate salt.

In another particular embodiment, preferred compounds are those wherein $R_1$ $CH_2OH$, $R_2$ is H, and the other substituents and indexes have the meanings reported above.

The preferred compound of said class is salmeterol, preferably in the form of a xinafoate salt.

The particle size of said microparticles is lower than 15 microns, preferably lower than 10 microns. Advantageously, at least 90% of the particles have a volume diameter lower than about 5 micron. More advantageously no more than 10% of the microparticles have a volume diameter [d(v,0.1)] lower than 0.6 micron, and no more than 50% of particles have a volume diameter [d(v,0.5)] lower than 1.5 micron.

Preferably the [d(v,0.5)] is comprised between 1.5 and 3.0 micron.

The particle size method could be measured by laser diffraction according to known methods.

The microparticles of the compound of general formula (I) are coated with a C12-C20 fatty acid in an amount comprised between 0.2 and 2.5% by weight of said particles, preferably between 0.5 and 2.0% by weight. In one embodiment, the preferred amount may be comprised between 1.0 and 2.0% by weight, while in other embodiment, it may be comprised between 0.5 and 1.0% by weight.

The C12-C20 fatty acid is advantageously selected from the group consisting of saturated and monounsaturated compounds such as lauric acid (C12:0), myristic acid (C14:0), palmitic acid (C16:0), palmitoleic acid (C16:1), stearic acid (C18:0), oleic acid (C18:1), and arachidic acid (C20:0) or mixtures thereof.

More preferably, the fatty acid it is a saturated fatty acid selected from the group consisting of myristic acid, palmitic acid, stearic acid, and arachidic acid. In a preferred embodiment, the fatty acid is myristic acid. In fact, the percentage being equal, myristic acid is capable of giving rise to higher performances in terms of respirable fraction (FPF) as it can be appreciated from the Examples.

As monounsaturated acid, oleic acid may be preferably used.

The fatty acid shall form a continuous film on the surface of the microparticles.

Depending on the amount of fatty acid, the coating may cover part of the microparticles or all of them (complete coating), preferably all of them.

The amount of $beta_2$-adrenergic agonist will depend on its single therapeutically effective dose, which in turn, depends on the kind and the severity of the disease and the conditions (weight, sex, age) of the patient.

For example, in the case of formoterol, the single therapeutically effective dose could be 6 or 12 µg, calculated as fumarate dihydrate salt.

Once the microparticles of the invention are suspended in a liquefied propellant gas, the relevant suspensions turned out to be chemically and physically stable over time and capable of giving rise to excellent respirable fraction. Unexpectedly, said formulations show a lower sedimentation speed than the corresponding formulations comprising uncoated microparticles.

Accordingly, the present invention provides for pressurized metered dose inhalers (pMDIs) comprising the above microparticles in suspension in a liquefied propellant gas. Any liquefied propellant gas may be used, preferably a hydrofluoroalkane (HFA) propellant. Advantageously, the liquefied propellant gas is 1,1,1,2,3,3,3-heptafluoro-n-propane (HFA227) or 1,1,1,2-tetrafluoroethane (HFA134a), and mixtures thereof.

The formulations of the present invention may also comprise other pharmaceutically acceptable excipients, for instance surfactants. Suitable surfactants are known in the art and include: sorbitan esters such as sorbitan trioleate, sorbitan monolaurate, sorbitan mono-oleate and their ethoxylated derivates such as polysorbate 20, polysorbate 80; ethylene oxide/propylene oxide co-polymers and other agents such as natural or synthetic lecithin, oleic acid, polyvinylpyrrolidone (PVP), and polyvinyl alcohol.

The amount of surfactant, which may be present in the pMDI formulation according to the invention, is usually in the range of 0.001 to 3.0% (w/w), preferably between 0.005 to 1.0% (w/w).

The formulations according to the present invention may further comprise other active ingredients useful for the prevention and/or treatment of respiratory diseases, for instance corticosteroids or antimuscarinic drugs suspended or dissolved in the liquefied propellant gas.

Examples of corticosteroids are beclometasone dipropionate (BDP), fluticasone propionate, fluticasone furoate, mometasone furoate, budesonide, and ciclesonide.

Examples of antimuscarinic drugs are ipratropium bromide, tiotropium bromide, glycopyrronium bromide, and aclidinium bromide.

According to another aspect, the present invention provides a pMDI comprising a canister filled with the pharmaceutical formulation of the invention and a metering valve for delivering a daily therapeutically effective dose of the active ingredient.

The aerosol formulation according to the invention shall be filled into pMDIs.

Said pMDIs comprise a canister fitted with a metering valve. Actuation of the metering valve allows a small portion of the spray product to be released.

Part or all of the internal surfaces of the canister may be made of glass or of a metal, for example aluminum or stainless steel or anodized aluminum.

Alternatively the metal canister may have part or all of the internal surfaces lined with an inert organic coating. Examples of preferred coatings are epoxy-phenol resins, perfluorinated polymers such as perfluoroalkoxyalkanes, perfluoroalkoxyalkylenes, perfluoroalkylenes such as polytetrafluoroethylene (Teflon), fluorinated-ethylene-propylene, polyether sulfone, fluorinated-ethylene-propylene (FEP), and fluorinated-ethylene-propylene polyether sulfone (FEP-PES) mixtures or combination thereof. Other suitable coatings may be polyamide, polyimide, polyamideimide, polyphenylene sulfide or their combinations.

The canister is closed with a metering valve for delivering a daily therapeutically effective dose of the active ingredient.

Generally, the metering valve assembly comprises a ferrule having an aperture formed therein, a body molding attached to the ferrule which houses the metering chamber, a stem constituted of a core and a core extension, an inner- and an outer seal around the metering chamber, a spring around the core, and a gasket to prevent leakage of propellant through the valve.

The gasket may comprise any suitable elastomeric material such as, for example, low density polyethylene, chlorobutyl, black and white butadiene-acrylonitrile rubbers, butyl rubber, neoprene, EPDM (a polymer of ethylenepropylenediene monomer) and TPE (thermoplastic elastomer). EPDM rubbers are particularly preferred.

Suitable valves are commercially available from manufacturers well known in the aerosol industry, for example, from Valois, France, Bespak, plc UK and 3M, Neotechnic Ltd UK.

The formulation shall be actuated by a metering valve capable of delivering a volume of between 25 µl and 100 µl, e.g. 25 µl, 50 µl, 63 µl or 100 µl.

Advantageously, the MDI device filled with the formulation may be equipped with a dose counter.

Surprisingly, when administered as a powder by a suitable device, the microparticles of the inventions give rise to a significantly higher respirable fraction than the corresponding uncoated microparticles.

Accordingly, the invention also provides a dry powder pharmaceutical formulation comprising the above microparticles and optionally a carrier.

The carrier particles may be made of any physiologically acceptable, pharmacologically inert material or combination of materials suitable for inhalatory use. For example, the carrier particles may be composed of one or more materials selected from sugar alcohols; polyols, for example sorbitol, mannitol and xylitol, and crystalline sugars, including monosaccharides and disaccharides.

Preferably, the carrier particles are made of lactose, more preferably of alpha-lactose monohydrate.

Advantageously, said carrier particles have a mass diameter (MD) of at least 50 microns, more advantageously greater that 90 microns. Preferably the MD is comprised between 50 microns and 500 microns.

In certain embodiments of the invention, the MD may be comprised between 90 and 150 microns.

In other embodiments, the MD may be comprised between 150 and 400 micron, with a MMD preferably greater than 175 microns, and more preferably the MD may be comprised between 210 and 355 microns.

The desired particle size may be obtained by sieving according to known methods.

The aforementioned powder formulation may also advantageously comprise an additive material, preferably bound to the surface of the carrier particles. Said additive material may be an amino acid, preferably selected from leucine or isoleucine, or a water soluble surface active material, for example lecithin, in particular soya lecithin, or a lubricant selected from the group consisting of stearic acid and salts thereof such as magnesium stearate, sodium lauryl sulphate, sodium stearyl fumarate, and stearyl alcohol.

The dry powder formulations herein described may be used in all customary dry powder inhalers, such as unit dose or multidose inhalers.

For example, said formulations may be filled in hard gelatine capsules, in turn loaded in a unit dose inhaler such as the Aerolizer™ or the RSO1/7 model available from Plastiape, Italy.

Alternatively, it may be filled in a multidose inhaler comprising a powder reservoir as described in WO 2004/012801, which is incorporated herein by reference in its entirety.

The present invention further provides a process for preparing the microparticles of the invention, said process comprising the steps of:

(a) preparing a solution of the C12-C20 fatty acid in a fluorinated model propellant wherein the beta2-agonist is substantially insoluble selected from the group of perfluoropentane, 2H,3H-perfluoropentane (HPFP), perfluorohexane, and 1H-perfluorohexane;

(b) adding the micronized drug powder to the solution of the fatty acid;

(c) mixing to give a homogeneous suspension; and (d) subjecting the resulting suspension to spray-drying to obtain the coated microparticles.

It fact, it has been found that, due to the physico-chemical properties of the utilized model propellant, the solid characteristic of the particles upon drying are not modified, and they remain substantially crystalline. Advantageously, the microparticles of the present invention have a crystalline degree, expressed as weight % of the crystalline compound with respect to the total weight of the compound, of at least 90%, preferably of at least 95%, even more preferably of at least 98%, determined according to methods know in the art such as differential scanning calorimetry (DSC), microcalorimetry or X-ray powder diffractometry.

Moreover, since the fatty acid is added as a solution, a uniform and extensive coating of microparticles is achieved. Said coating with the fatty acid is performed in the absence of any other coating excipient.

Without being limited by the theory, said uniform and extensive coating may contribute to improve the chemical stability of the active ingredient. Furthermore, it prevents both the partial solubilization and formation of aggregates of the drug, once suspended in a liquefied propellant gas, making possible to obtain formulations characterized by an improved physical stability.

It is believed that the features of the coating explain the better inhalatory performances of the microparticles of the invention, once administered as a powder, in comparison to the uncoated microparticles.

The fluorinated model propellant shall be selected depending on the solubility characteristics of both the active ingredient and the fatty acid.

Preferably, said model propellant is perfluoropentane or 2H,3H-perfluoropentane (HPFP), more preferably 2H,3H-perfluoropentane.

The amount of the fatty acid in the solution will vary depending on the amount of active ingredient added in stage (b) and will be selected so as to obtain a percentage in the final coated microparticles comprised between 0.2 and 2.5% by weight.

The content of the active ingredient in the suspension prepared in stage (b) can vary within wide limits, usually within the range from 1 to 40% w/v, preferably from 2 to 20% w/v, more preferably from 5 to 10% w/v.

In said stage, the micronized drug powder may be added to the solution of the fatty acid and then mixed with techniques known in the art, e.g. sonicating or stirring, to give a homogeneous suspension (stage (c).

In stage (d), the obtained suspension, maintained under stirring, is subjected to spray drying in an appropriate apparatus.

The operating parameters of the apparatus, such as the flow rate of the suspension arriving in the drying chamber, the size of the nozzle, the inlet and outlet temperature, the atomizing pressure and the flow rate of the atomizing air, may be adjusted by any skilled person according to the recommendations of the manufacturer.

A suitable spray dryer is, for example, the Büchi 191 Mini Spray Dryer (Büchi Company, Switzerland).

Typical parameters are the following:

inlet air temperature: 60 to 150° C., preferably 95 to 105° C., more preferably 100° C.;

outlet temperature: 40 to 110° C., preferably 55 to 65° C., more preferably 60° C.;

air flow rate: 6001/h;

feed flow: 4 ml/min; and nozzle diameter: 0.7 mm.

Once collected, the microparticles have a diameter less than 15 micron.

Optionally, they may be subjected to conventional milling techniques to adjust their size.

Administration of the microparticles of the invention may be indicated for prevention and/or the treatment of mild, moderate or severe acute or chronic symptoms or for prophylactic treatment of an inflammatory or obstructive airways disease such as asthma and chronic obstructive pulmonary disease (COPD).

Other features of the invention will become apparent in the course of the following descriptions of exemplary embodiments which are given for illustration of the invention and are not intended to be limiting thereof.

EXAMPLES

Example 1

Preparation of Microparticles of Formoterol Fumarate According to the Invention 5 mg of myristic acid were dissolved in 100 ml of 2H,3H-perfluoropentane at 30-35° C. in a water bath. 995 mg of formoterol fumarate dihydrate as micronized particles were added and dispersed, the suspension was sonicated and then kept under stirring. The suspension thus obtained contained 99.5% formoterol fumarate dihydrate and 0.5% myristic acid by weight.

This suspension was spray-dried in a Büchi 191 Mini Spray Dryer using the following parameters:

inlet air temperature: 100° C.;

outlet temperature: 60° C.;

air flow rate: 600 l/h;

feed flow: 4 ml/min; and nozzle diameter: 0.7 mm.

The yield of the process was 69.0%.

Analogously, formoterol fumarate dehydrate (FF) microparticles having the following compositions were obtained:

| Sample | FF (w/w %) | Additive (w/w %) | Yield (%) |
|---|---|---|---|
| FF-myr 1.0% | 99.0 | Myristic acid 1.0 | 70.3 |
| FF-myr 2.0% | 98.0 | Myristic acid 2.0 | 68.1 |
| FF-lau 0.5% | 99.5 | Lauric acid 0.5 | 68.4 |
| FF-pal 0.5% | 99.5 | Palmitic acid 0.5 | 69.3 |
| FF-ole 0.5% | 99.5 | Oleic acid 0.5 | 69.3 |

Example 2

Characterization of the Microparticles of Example 1

The microparticles as obtained in Example 1 were subjected to the following analysis.

Scanning electron microscopy (SEM). Morphological properties were investigated using a scanning electron microscope (SEM, Zeiss SUPRA 40, Oberkochen, Germany). Each sample was carefully mounted on a sample holder, so as to ensure representative images, and analyzed without coating sputter. SEM micrographs were taken using in-built image capture software. The obtained images demonstrate that the microparticles of the invention do not change their morphological aspect in comparison to the uncoated FF microparticles.

Differential scanning calorimetry (DSC). The crystalline properties were further investigated by differential scanning calorimetry (DSC). The data were obtained on a Mettler Toledo Instrument DSC821c, software STARe. The calibration standard used is indium. Approximately 2 to 5 mg of a sample is placed into a DSC pan, and the weight is accurately measured and recorded. The pan is hermetically sealed. The sample is heated under nitrogen at a rate of 20° C./min, from 25° C. to a final temperature of 200° C. The thermogram reported in FIG. 1 shows that the characteristic endothermic transition ending at about 160° C., typical of crystalline formoterol fumarate dihydrate, is still present in the microparticles of the invention, indicating that the spray-drying process has not modified the solid characteristics of the drug.

The microparticles coated with amounts of additive ranging from 1.0 to 2.0% w/v are more crystalline than microparticles coated with a lower amount, i.e. 0.5% w/v.

Particle size via laser diffraction. Particle size distributions were measured by laser diffraction (Spraytec® S, Malvern Instruments, Worcestershire, UK). The powders were dispersed in Span85:cyclohexane 0.1% w/v. The results are reported in Table 1. After spray-drying, the particle size of the microparticles of the invention does not substantially change in comparison to that of raw formoterol fumarate dihydrate.

TABLE 1

Particle size.

| Sample | d(v0.1) (μm) | d(v0.5) (μm) | d(v0.9) (μm) |
|---|---|---|---|
| FF raw material | 0.62 | 1.69 | 3.27 |
| FF-lau 0.5 | 0.86 | 1.96 | 3.60 |
| FF-myr 0.5 | 0.96 | 1.65 | 2.46 |
| FF-pal 0.5 | 0.85 | 1.84 | 3.48 |
| FF-ole 0.5 | 0.82 | 1.78 | 3.56 |

Example 3 pMDI Formulation Comprising the Microparticles of Example 1

To prepare pMDI aerosol suspension formulations with a nominal dose of the active ingredient of 12 μg, the aluminum canisters were filled in a controlled atmosphere room, by successively introducing 2.4 mg the microparticles of Example 1 and then 10 ml pressurized HFA134a gas. The devices were fitted with a 50 μl APTAR valve and a Bespak actuator of 0.3 mm. For comparative purposes, a pMDI aerosol suspension formulations comprising micronized formoterol fumarate dihydrate was also prepared. The sedimentation rate was determined using a Turbiscan apparatus (Formulaction SA, France).

The pMDI formulations obtained with microparticles of the invention exhibit a good homogenous distribution of the suspended particles as well as a higher level of physical stability than the comparative formulation, as the particles sediment more slowly and are less liable to form agglomerates.

The pMDI formulations were also characterized in terms of aerosol performances. They were assessed using a Next Generation Impactor to according to the procedure described in the European Pharmacopoeia $7^{th}$ edition, 2011, part 2.9.18.

Quantification of formoterol fumarate dihydrate (FF) was performed using a HPLC method. The following parameters were determined:

i) delivered dose (DD) is calculated from the cumulative deposition in the ACI, divided by the number of actuations per experiment;

ii) fine particle mass (FPM) is obtained by interpolation of the cumulative percentage undersize of drug mass deposition versus cut off diameter. The FPM corresponds to particles of diameter ≤5.0 microns, divided by the number of actuations per experiment.

iii) respirable fraction (fine particle fraction=FPF) which is the percent ratio between the fine particle mass and the delivered dose.

iv) mass median aerodynamic diameter (MMAD) which is the diameter around which the mass aerodynamic diameters of the emitted particles are distributed equally;

The results (as a mean±S.D.) are summarized in Table 2. It is evident that the PMDI formulations comprising the microparticles of the invention give rise to an excellent respirable fraction, comparable to that of the formulation comprising uncoated micronized FF.

TABLE 2

Aerosol performances of the pMDI formulations.

| Sample | DD (μg) | MMAD (μm) | FPM (μg) | FPF (%) |
|---|---|---|---|---|
| FF-Raw | 8.34 ± 0.32 | 1.92 ± 0.00 | 6.84 ± 0.51 | 81.9 ± 2.9 |
| FF-Lau 0.5 | 7.10 ± 0.22 | 2.07 ± 0.13 | 5.35 ± 0.11 | 75.4 ± 0.8 |
| FF-Pal 0.5 | 8.12 ± 0.35 | 2.20 ± 0.01 | 6.30 ± 0.14 | 77.7 ± 1.6 |
| FF-Ole 0.5 | 8.56 ± 0.33 | 2.10 ± 0.10 | 6.85 ± 0.42 | 80.1 ± 1.8 |
| FF-Mir0.5 | 8.23 ± 0.23 | 2.45 ± 0.01 | 5.12 ± 0.21 | 62.2 ± 0.7 |
| FF-Mir 1 | 8.21 ± 0.25 | 2.18 ± 0.08 | 6.46 ± 0.39 | 78.7 ± 2.3 |
| FF-Mir 2 | 8.69 ± 0.07 | 2.05 ± 0.03 | 7.31 ± 0.02 | 84.1 ± 0.5 |

Example 4

Powder Formulation Comprising Formoterol Fumarate Microparticles According to the Invention To prepare powder formulations, the microparticles of Example 1 FF-myr 0.5 and Ff-myr 2.0 were mixed in a Turbula mixer with alpha-lactose monohydrate having a mass diameter comprised between 90 and 150 μm as a carrier, to obtain a ratio of 6 μg of drug to 10 mg of carrier. For comparative purposes, a powder formulation comprising micronized formoterol fumarate dihydrate was also prepared. Each powder was filled in hard HMPC gelatine capsules, in turn loaded in a RS01/7 unit dose inhaler (Plastiape, Italy).

The aerosol performances were evaluated using a Next Generation Impactor (NGI) according to the procedure described in European Pharmacopoeia $7^{th}$ edition, 2011, part 2.9.18, pages 281-285. The results (mean±S.D.) in terms of delivered dose (DD), fine particle mass (FPM), fine particle fraction (FPF) and mass median aerodynamic diameter (MMAD), are reported in Table 3. The data demonstrate that the powder formulations comprising the microparticles of the invention give rise to significantly higher respirable fractions than that comprising uncoated micronized FF.

TABLE 3

Aerosol performances of the powder formulations.

| Sample | DD μg | FPM μg | FPF % | MMAD μm |
|---|---|---|---|---|
| FF raw4. | 73 ± 0.02 | 0.71 ± 0.04 | 14.03 ± 0.82 | 2.36 ± 0.05 |
| FF-myr 0.5 | 4.41 ± 0.01 | 1.17 ± 0.04 | 26.47 ± 1.02 | 1.85 ± 0.03 |
| FF-myr 2.0 | 4.69 ± 0.30 | 1.09 ± 0.06 | 23.35 ± 0.25 | 1.65 ± 0.02 |

Example 5

Preparation of Microparticles of Salmeterol Xinafoate According to the Invention 10 mg of myristic acid were dissolved in 100 ml of 2H,3H-perfluoropentane at 30-35° C. in a water bath. 990 mg of salmeterol xinafoate (SX) as micronized particles were added and dispersed, the suspension was sonicated and then kept under stirring. The suspension thus obtained contained 99% formoterol fumarate dihydrate and 1.0% myristic acid by weight. This suspension was spray-dried in a Büchi 191 Mini Spray Dryer with the following parameters:

inlet air temperature: 100° C.;
outlet temperature: 64° C.;
air flow rate: 600 l/h;
feed flow: 4 ml/min; and
nozzle diameter: 0.7 mm.

Analogously, SX microparticles with oleic acid were prepared. The microparticles have the following composition:

| Sample | FF (w/w %) | Additive (w/w %) | Yield (%) |
|---|---|---|---|
| SX-myr 1.0% | 99.0 | Myristic acid 1.0 | 75.0 |
| SX-ole 2.0% | 98.0 | Oleic acid 1.0 | 85.0 |

Example 6 pMDI Formulation Comprising the Microparticles of Example 5

To prepare pMDI aerosol suspension formulations with a nominal dose of the active ingredient of 25 µg, canisters coated with FEP were filled in a controlled atmosphere room, by successively introducing 3.0 mg the microparticles of Example 5 and then 6 ml pressurized HFA134a gas. The devices were fitted with a 50 µl APTAR valve and a Bespak actuator of 0.3 mm. For comparative purposes, a pMDI aerosol suspension formulations comprising micronized salmeterol xinafoate was also prepared. The pMDI formulations were characterized in terms of aerosol performances. They were assessed as described in Example 3. The results (as a mean±S.D.) are summarized in Table 4.

It is evident that the PMDI formulations comprising the microparticles of the invention give rise to a satisfactory respirable fraction, slightly better to that of the formulation comprising uncoated micronized.

TABLE 4

Aerosol performances of the pMDI formulations.

| Sample | DD µg | FPM µg | FPF % | MMAD µm |
|---|---|---|---|---|
| SX raw | 14.28 ± 1.72 | 4.23 ± 0.25 | 29.74 ± 1.75 | 2.79 ± 0.39 |
| SX-ole 1.0 | 16.73 ± 2.09 | 5.82 ± 0.83 | 34.77 ± 2.32 | 3.02 ± 0.06 |
| SX-myr 1.0 | 22.43 ± 0.76 | 6.77 ± 0.57 | 39.55 ± 4.06 | 2.46 ± 0.07. |

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing chemically stable crystalline microparticles, comprising formoterol fumarate dihydrate coated with myristic acid in an amount of 1.0 to 2.0% by weight based on a total weight of the crystalline microparticles, the process comprising:
   (a) preparing a solution of myristic acid in a fluorinated model propellant in which the formoterol fumarate dihydrate is substantially insoluble, selected from the group consisting of perfluoropentane, 2H,3H-perfluoropentane (HPFP), perfluorohexane, and 1H-perfluorohexane;
   (b) adding the formoterol fumarate dihydrate as a micronized powder to the solution of myristic acid, to obtain a mixture;
   (c) mixing the mixture to obtain a homogeneous suspension;
   (d) subjecting the suspension to spray-drying, to obtain the coated microparticles, the myristic acid forming a continuous film on a surface of the microparticles;
   (e) preparing a pharmaceutical aerosol formulation comprising the coated microparticles in suspension in a liquefied propellant gas; and
   (f) filling the pharmaceutical aerosol formulation into a pressurized metered dose inhaler.

2. The process according to claim 1, wherein the fluorinated model propellant is 2H,3H-perfluoropentane (HPFP).

3. The process according to claim 1, wherein the liquefied propellant gas is 1,1,1,2,3,3,3-heptafluoro-n-propane (HFA227) or 1,1,1,2-tetrafluoroethane (HFA 134a), or a mixture thereof.

* * * * *